(12) United States Patent  (10) Patent No.: US 7,476,254 B2
White et al.  (45) Date of Patent: Jan. 13, 2009

(54) COMPLIANT FIXATION FOR PELVIS

(75) Inventors: John R White, Winona Lake, IN (US); David R Brown, Warsaw, IN (US)

(73) Assignee: Biomet Manufacturing Corporation, Warsaw, IN (US)

( * ) Notice: Subject to any disclaimer, the term of this patent is extended or adjusted under 35 U.S.C. 154(b) by 75 days.

(21) Appl. No.: 11/326,561

(22) Filed: Jan. 5, 2006

(65) Prior Publication Data

US 2006/0116775 A1    Jun. 1, 2006

Related U.S. Application Data

(63) Continuation-in-part of application No. 10/838,885, filed on May 4, 2004, and a continuation-in-part of application No. 10/797,692, filed on Mar. 9, 2004, now Pat. No. 7,141,073, which is a continuation-in-part of application No. 10/305,620, filed on Nov. 27, 2002, now Pat. No. 6,712,855, which is a continuation of application No. 09/776,584, filed on Feb. 2, 2001, now Pat. No. 6,508,841, which is a continuation of application No. 09/003,061, filed on Jan. 5, 1998, now Pat. No. 6,197,065, which is a continuation-in-part of application No. 08/535,532, filed on Sep. 28, 1995, now abandoned, which is a continuation-in-part of application No. 08/146,510, filed on Nov. 1, 1993, now abandoned.

(51) Int. Cl.
    *A61F 2/32* (2006.01)
(52) U.S. Cl. ............... 623/22.32; 623/22.37; 623/22.38
(58) Field of Classification Search ..... 623/22.21–22.4, 623/23.21, 23.22, 23.24, 23.25, 23.26, 23.35, 623/22.15
    See application file for complete search history.

(56) References Cited

U.S. PATENT DOCUMENTS

| 408,080 | A | 7/1889 | Carroll |
| 583,455 | A | 6/1897 | Bush |
| 1,217,637 | A | 2/1917 | Rink |
| 2,397,545 | A | 4/1946 | Hardinge |
| 3,067,740 | A | 12/1962 | Haboush |
| 3,740,769 | A | 6/1973 | Haboush |
| 3,947,897 | A | 4/1976 | Owens |
| 4,016,874 | A | 4/1977 | Maffei et al. |

(Continued)

FOREIGN PATENT DOCUMENTS

DE    3605630    9/1987

(Continued)

OTHER PUBLICATIONS

"D.L.Martin, M.D., A.S. Turner, B. V.Sc., M.S., J.O. Johnston, M.D. ;" Comparison of Cortical Bone Loss in Segmental Bone Prosthetic Replacement: Cemented Stem vs. Compliant Fixation.

(Continued)

*Primary Examiner*—Bruce E Snow
(74) *Attorney, Agent, or Firm*—Harness, Dickey & Pierce, P.L.C.

(57) ABSTRACT

A pelvic implant assembly and associated methods. The implant assembly includes an acetabular component, and a compliant fixator coupling the acetabular component to the pelvis.

11 Claims, 6 Drawing Sheets

U.S. PATENT DOCUMENTS

| | | | |
|---|---|---|---|
| 4,080,666 A | 3/1978 | Fixel | |
| 4,129,903 A | 12/1978 | Huggler | |
| 4,158,895 A | 6/1979 | Reswick et al. | |
| 4,245,360 A | 1/1981 | Brinckmann et al. | |
| 4,262,665 A | 4/1981 | Roalstad et al. | |
| 4,314,381 A | 2/1982 | Koeneman | |
| 4,502,160 A | 3/1985 | Moore et al. | |
| 4,547,912 A | 10/1985 | Sherva-Parker | |
| 4,586,932 A | 5/1986 | Scales | |
| 4,623,352 A | 11/1986 | Oh | |
| 4,644,943 A | 2/1987 | Thompson et al. | |
| 4,673,407 A * | 6/1987 | Martin | 623/20.33 |
| 4,682,590 A | 7/1987 | Kothmann | |
| 4,781,720 A | 11/1988 | Sherva-Parker | |
| 4,822,366 A | 4/1989 | Bolesky | |
| 4,827,918 A | 5/1989 | Olerud et al. | |
| 4,883,489 A | 11/1989 | Grundei et al. | |
| 4,892,551 A | 1/1990 | Haber | |
| 4,904,264 A | 2/1990 | Scheunemann | |
| 4,923,472 A | 5/1990 | Ugolini | |
| 4,938,768 A | 7/1990 | Wu | |
| 4,946,459 A | 8/1990 | Bradshaw et al. | |
| 4,947,502 A | 8/1990 | Engelhardt | |
| 4,955,910 A | 9/1990 | Bolesky | |
| 4,959,064 A | 9/1990 | Engelhardt | |
| 4,959,072 A | 9/1990 | Morscher et al. | |
| 4,986,834 A | 1/1991 | Smith et al. | |
| 5,007,935 A | 4/1991 | Vincent et al. | |
| 5,007,936 A | 4/1991 | Woolson | |
| 5,030,220 A | 7/1991 | Howland | |
| 5,035,712 A | 7/1991 | Hoffman | |
| 5,057,103 A | 10/1991 | Davis | |
| 5,071,435 A | 12/1991 | Fuchs et al. | |
| 5,108,398 A | 4/1992 | McQueen et al. | |
| 5,112,333 A | 5/1992 | Fixel | |
| 5,133,760 A | 7/1992 | Petersen et al. | |
| 5,156,625 A * | 10/1992 | Marchetti et al. | 623/22.33 |
| 5,180,383 A | 1/1993 | Haydon | |
| 5,181,928 A | 1/1993 | Bolesky et al. | |
| 5,197,989 A | 3/1993 | Hinckfuss et al. | |
| 5,201,881 A | 4/1993 | Evans | |
| 5,267,999 A | 12/1993 | Olerud et al. | |
| 5,281,226 A | 1/1994 | Davydov et al. | |
| 5,326,360 A | 7/1994 | Kotz et al. | |
| 5,326,367 A | 7/1994 | Robioneck | |
| 5,326,368 A | 7/1994 | Collazo | |
| 5,334,184 A | 8/1994 | Bimman | |
| 5,352,227 A | 10/1994 | O'Hara | |
| 5,356,410 A | 10/1994 | Pennig et al. | |
| 5,358,524 A | 10/1994 | Richelsoph | |
| 5,389,107 A | 2/1995 | Nassar et al. | |
| 5,411,504 A | 5/1995 | Vilas | |
| 5,507,747 A | 4/1996 | Yuan et al. | |
| 5,507,827 A | 4/1996 | Grundei et al. | |
| 5,549,692 A | 8/1996 | Hauser et al. | |
| 5,658,288 A | 8/1997 | Kim | |
| 5,743,908 A | 4/1998 | Kim | |
| 5,800,553 A | 9/1998 | Albrektsson et al. | |
| 5,800,557 A | 9/1998 | Elhami | |
| 5,824,078 A | 10/1998 | Nelson et al. | |
| 5,827,285 A | 10/1998 | Bramlet | |
| 5,871,540 A | 2/1999 | Weissman et al. | |
| 5,871,548 A * | 2/1999 | Sanders et al. | 623/22.36 |
| 5,882,351 A | 3/1999 | Fox | |
| 5,916,268 A * | 6/1999 | Schollner et al. | 623/22.36 |
| 5,928,232 A | 7/1999 | Howland et al. | |
| 5,941,881 A | 8/1999 | Barnes | |
| 5,951,555 A | 9/1999 | Rehak et al. | |
| 5,981,828 A | 11/1999 | Nelson et al. | |
| 6,051,007 A | 4/2000 | Hogendijk et al. | |
| 6,162,257 A | 12/2000 | Gustilo et al. | |
| 6,197,065 B1 | 3/2001 | Martin et al. | |
| 6,200,317 B1 | 3/2001 | Aalsma et al. | |
| 6,273,891 B1 | 8/2001 | Masini | |
| 6,293,971 B1 | 9/2001 | Nelson et al. | |
| 6,336,929 B1 | 1/2002 | Justin | |
| 6,336,941 B1 | 1/2002 | Subba Rao et al. | |
| 6,387,097 B1 | 5/2002 | Alby et al. | |
| 6,458,161 B1 | 10/2002 | Gibbs et al. | |
| 6,482,238 B1 | 11/2002 | Grundei | |
| 6,485,522 B1 | 11/2002 | Grundei | |
| 6,508,841 B2 | 1/2003 | Martin et al. | |
| 6,579,294 B2 | 6/2003 | Robioneck | |
| 6,656,184 B1 | 12/2003 | White et al. | |
| 6,712,855 B2 | 3/2004 | Martin et al. | |
| 6,740,089 B2 | 5/2004 | Haider | |
| 6,786,910 B2 | 9/2004 | Cohen et al. | |
| 6,840,959 B2 | 1/2005 | Treacy et al. | |
| 2001/0051831 A1 | 12/2001 | Subba Rao et al. | |
| 2003/0028249 A1 | 2/2003 | Baccelli et al. | |
| 2003/0109878 A1 | 6/2003 | Grundei | |
| 2003/0130659 A1 | 7/2003 | Haider | |
| 2003/0195636 A1 | 10/2003 | Coop | |
| 2004/0138663 A1 | 7/2004 | Kosashvili et al. | |
| 2004/0148021 A1 | 7/2004 | Cartledge et al. | |
| 2004/0172138 A1 | 9/2004 | May et al. | |
| 2006/0241779 A1 * | 10/2006 | Lakin | 623/22.15 |

FOREIGN PATENT DOCUMENTS

| | | |
|---|---|---|
| DE | 293485 | 9/1991 |
| DE | 19931882 | 5/2001 |
| FR | 2519248 | 12/1981 |
| FR | 2519248 | 7/1983 |
| SU | 1181652 | 9/1985 |
| WO | WO96/35387 | 11/1996 |
| WO | WO98/29058 | 7/1998 |
| WO | WO00/27298 | 5/2000 |
| WO | WO01/43652 | 6/2001 |
| WO | WO02/071962 | 9/2002 |

OTHER PUBLICATIONS

"Compression Nailing of Long Bones," Mueckley, et al., European Journal of Trauma 2003, No. 3, copyright Urban & Vogel.

Aboulafia, Albert J., et al., "Reconstruction Using the Saddle Prosthesis Following Excision of Primary and Metastic Periacetabular Tumors" (1995), Clinical Orthopaedics and Related Research, No. 314, pp. 203-213.

Satcher, Jr., Robert, et al., "Reconstruction of the Pelvis After Resection of Tumors About the Acetabulum", (2003), Clinical Orthopaedics and Related Research, No. 409, pp. 209-217.

European Search Report mailed Jul. 21, 2005 for pending European Application No. EP05251364.

* cited by examiner

COMPLIANT FIXATION FOR PELVIS

CROSS REFERENCE TO RELATED APPLICATIONS

This application is a continuation-in-part of U.S. patent application Ser. No. 10/797,692 filed Mar. 9, 2004, which is a continuation-in-part of U.S. patent application Ser. No. 10/305,620, filed Nov. 27, 2002, now U.S. Pat. No. 6,712,855, which is a continuation of U.S. patent application Ser. No. 09/776,584, filed Feb. 2, 2001, now U.S. Pat. No. 6,508,841, which is a continuation of U.S. patent application Ser. No. 09/003,061, filed Jan. 5, 1998, now U.S. Pat. No. 6,197,065, which is a continuation-in-part of U.S. patent application Ser. No. 08/535,532, filed Sep. 28, 1995, now abandoned, which is a continuation-in-part of U.S. patent application Ser. No. 08/146,510, filed Nov. 1, 1993, now abandoned. This application is also a continuation-in-part of U.S. patent application Ser. No. 10/838,885, filed May 4, 2004. The disclosures of all the above applications are incorporated herein by reference.

INTRODUCTION

Certain medical and treatment conditions result in extensive loss of acetabular bone, such as revision/reconstruction total hip replacements, periacetabular resections to remove pelvic tumors, osteoporotic fractures, trauma or other injuries. Various limb-sparing procedures utilize pelvic prostheses to address the resulting pelvic bone loss and/or reconstruct the damaged portion of the pelvis.

Although the existing pelvic prostheses can be satisfactory for their intended purposes, there is still a need for pelvic implants that can address these and other pelvic conditions.

SUMMARY

The present teachings provide a pelvic implant assembly and associated methods. The implant assembly includes an acetabular component, and a compliant fixator coupling the acetabular component to the pelvis.

The present teachings provide a method for attaching an implant to a pelvis. The method includes attaching a compliant fixator to the pelvis, and coupling an acetabular component to the compliant fixator.

The present teaching provide a pelvic implant assembly that includes an acetabular cup, a prosthetic femoral head coupled to the acetabular cup, a prosthetic femoral stem coupled to the femoral head, and a compliant fixator coupling the acetabular cup to the pelvis.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1b is a detail view of a portion of the pelvic implant assembly of FIG. 1a;

FIG. 2b is a detail view of a portion of the pelvic implant assembly of FIG. 2a;

DETAILED DESCRIPTION

The following description is merely exemplary in nature and is in no way intended to limit the invention, its application, or uses. For example, although the implants of the present teachings are illustrated in connection with one side of a human pelvis, the present teachings can be used for implants in either or both sides of a human or other mammalian pelvis. The present teachings can be used in primary, revision, or reconstruction surgeries associated with the pelvis.

Figure 1A:
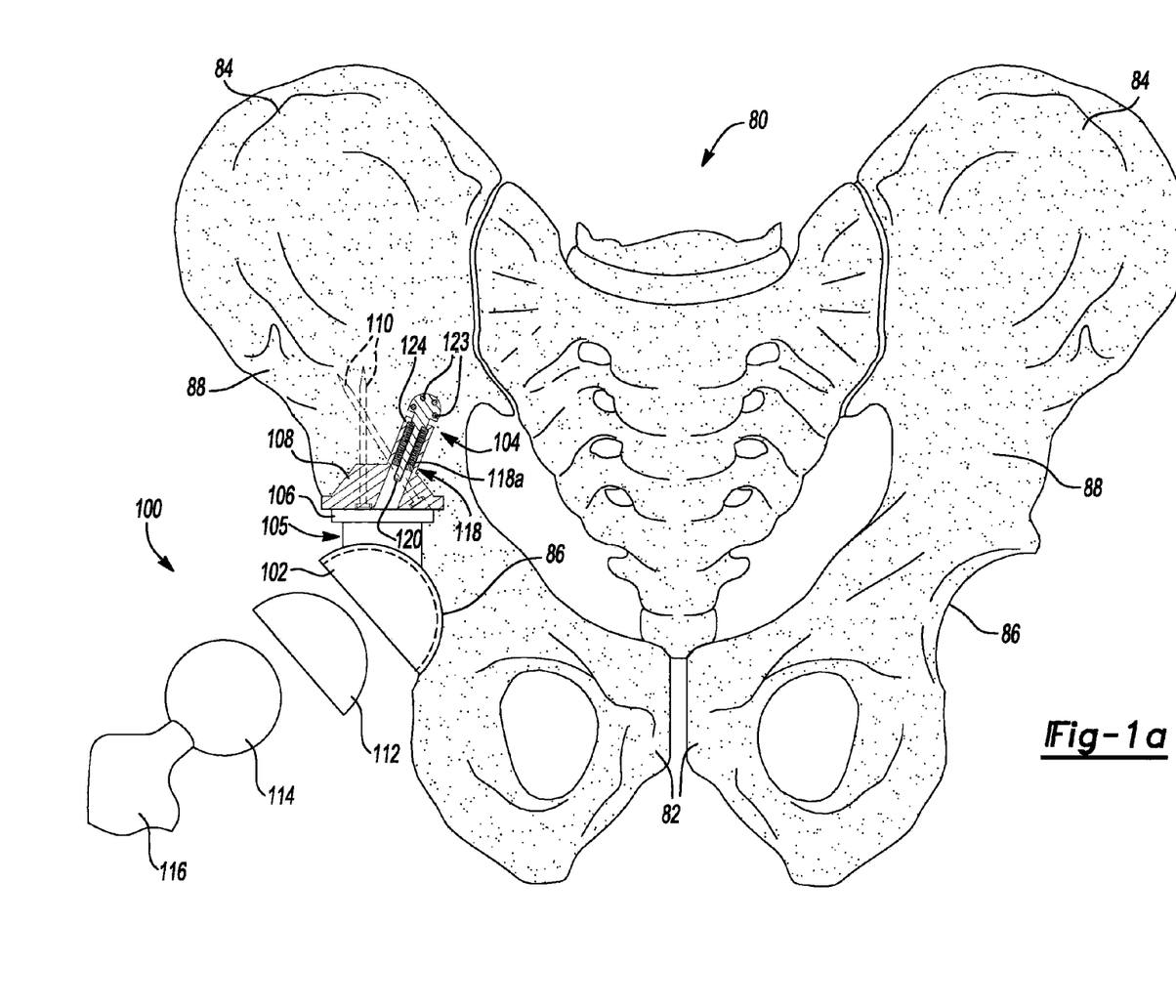
FIG. 1a is an environmental front view of a pelvic implant assembly according to the present teachings.

Referring to FIG. 1a, an exemplary pelvic implant assembly 100 according to the present teachings is illustrated attached to a portion of a pelvis 80, which generally includes an ilium 84, an ischium 88, a pubis with pubic bones 82, and an acetabulum 86. The prosthetic assembly 100 can replace portions of damaged bone on either side or both sides of the pelvis 80.

Referring to FIGS. 1a-2b, the exemplary pelvic implant assembly 100 can include an acetabular component 102, and a compliant fixator 104 that connects the acetabular component 102 to the ilium 84. The compliant fixator 104 provides a dynamic load to the ilium 84, such as, for example, a biased compressive load. The compliant fixator 104 can be implanted in a selected area of the ilium 84 at a selected orientation. The position and orientation of the compliant fixator 104 is not limited to the one illustrated herein, but can be selected on the basis of various factors, including the location and availability of healthy bone mass, location requirements for compressive load and bone growth promotion, and considerations of interaction with the acetabular component 102, balancing of the pelvis 80, and functioning of the associated hip joint.

The compliant fixator 104 can be any fixator configured to provide a bone biasing force to a portion of a pelvic bone, and in particular to the ilium 84. Any known compliant fixator 104 can be used, including, but not limited to, the compliant fixators disclosed in co-pending U.S. patent application Ser. No. 10/797,692, or related U.S. Pat. Nos. 6,712,855, 6,508,841, 6,197,065, all of which are assigned to common assignee Biomet, Inc. of Warsaw, Ind., and are incorporated herein by reference. The compliant fixator 104 is adapted to provide a compressive load on the pelvic bone, thereby reducing bone loss and promoting bone growth.

Figure 1B:
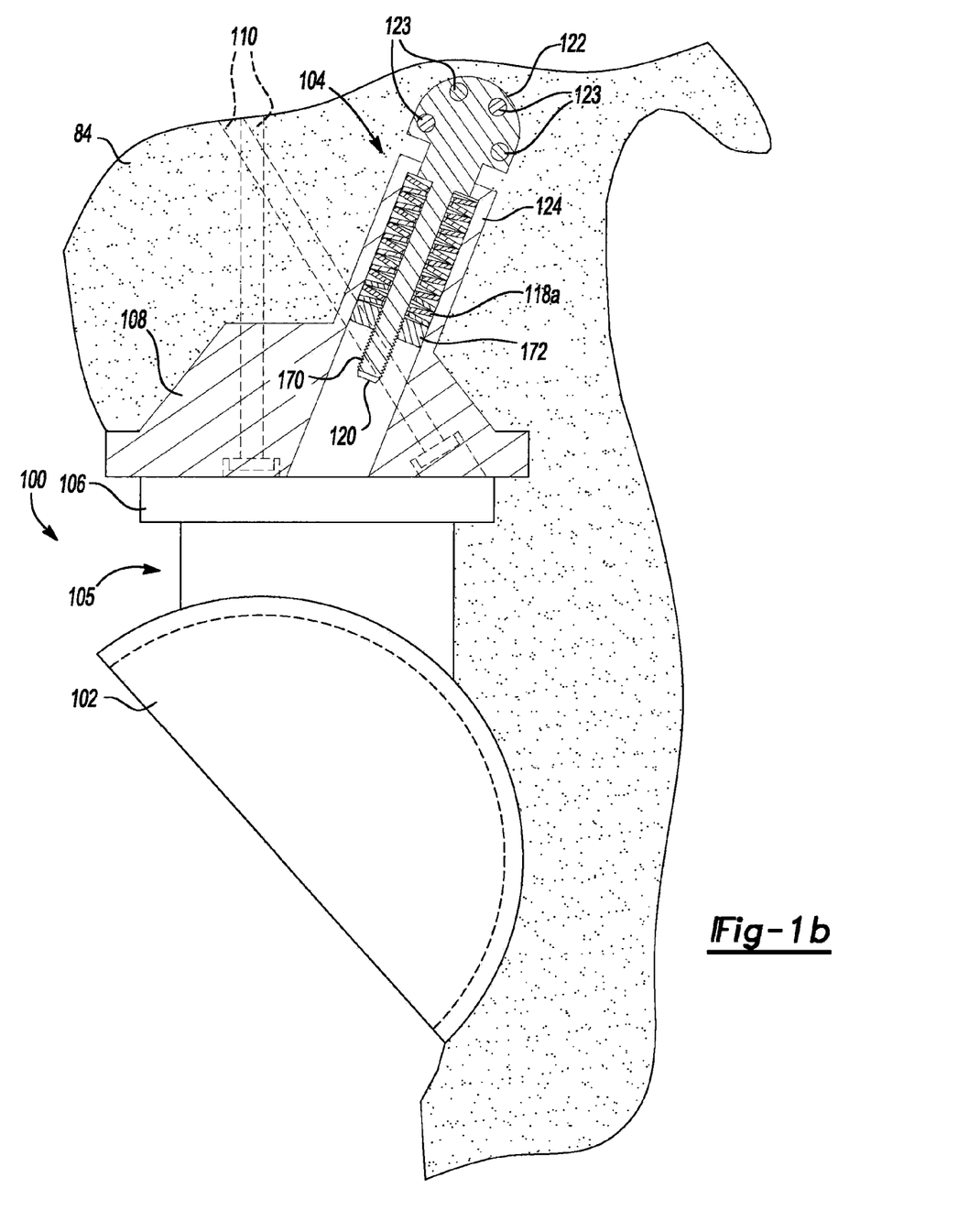
Figure 2A:
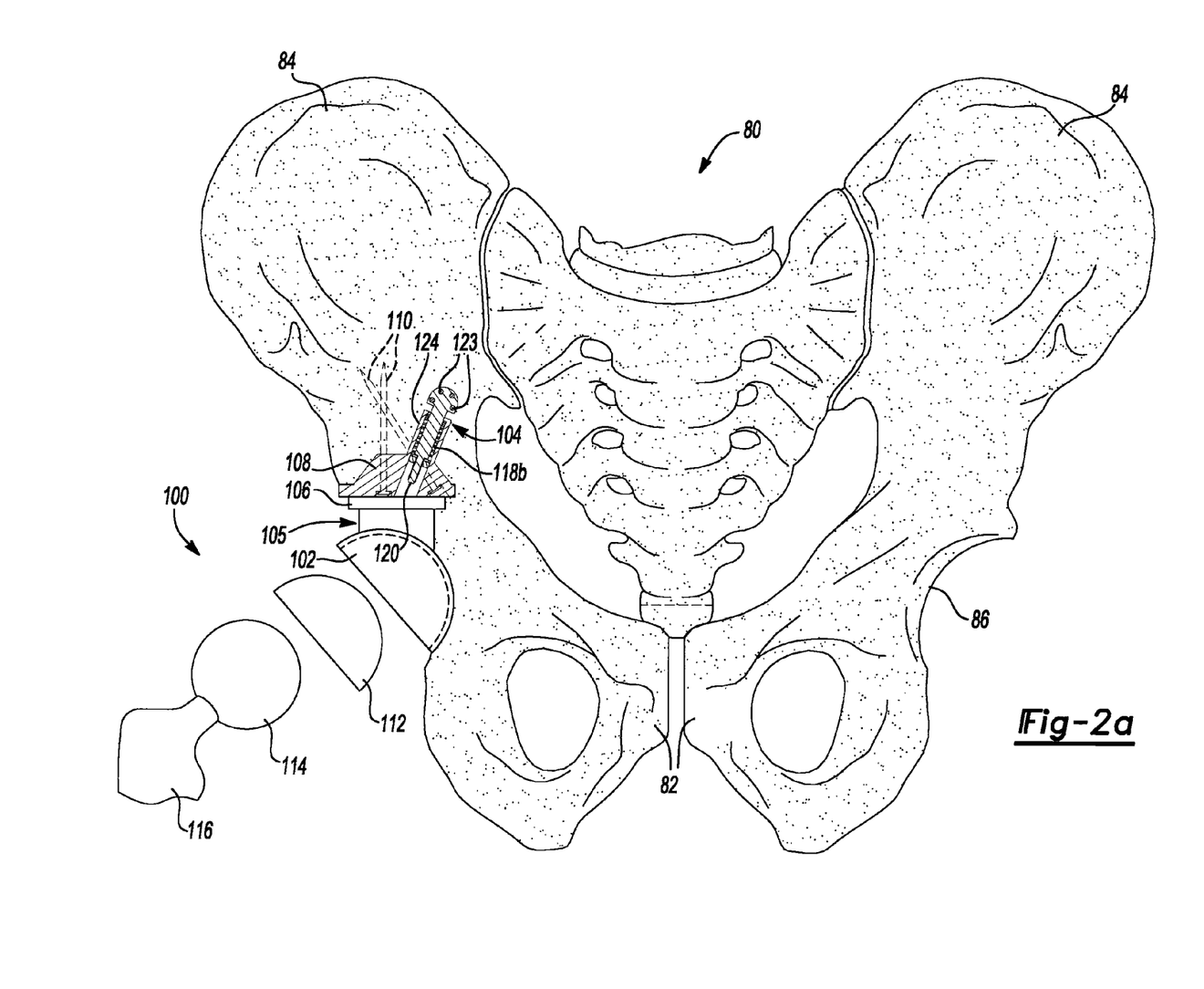
FIG. 2a is an environmental front view of a pelvic implant assembly according to the present teachings.
Figure 2B:
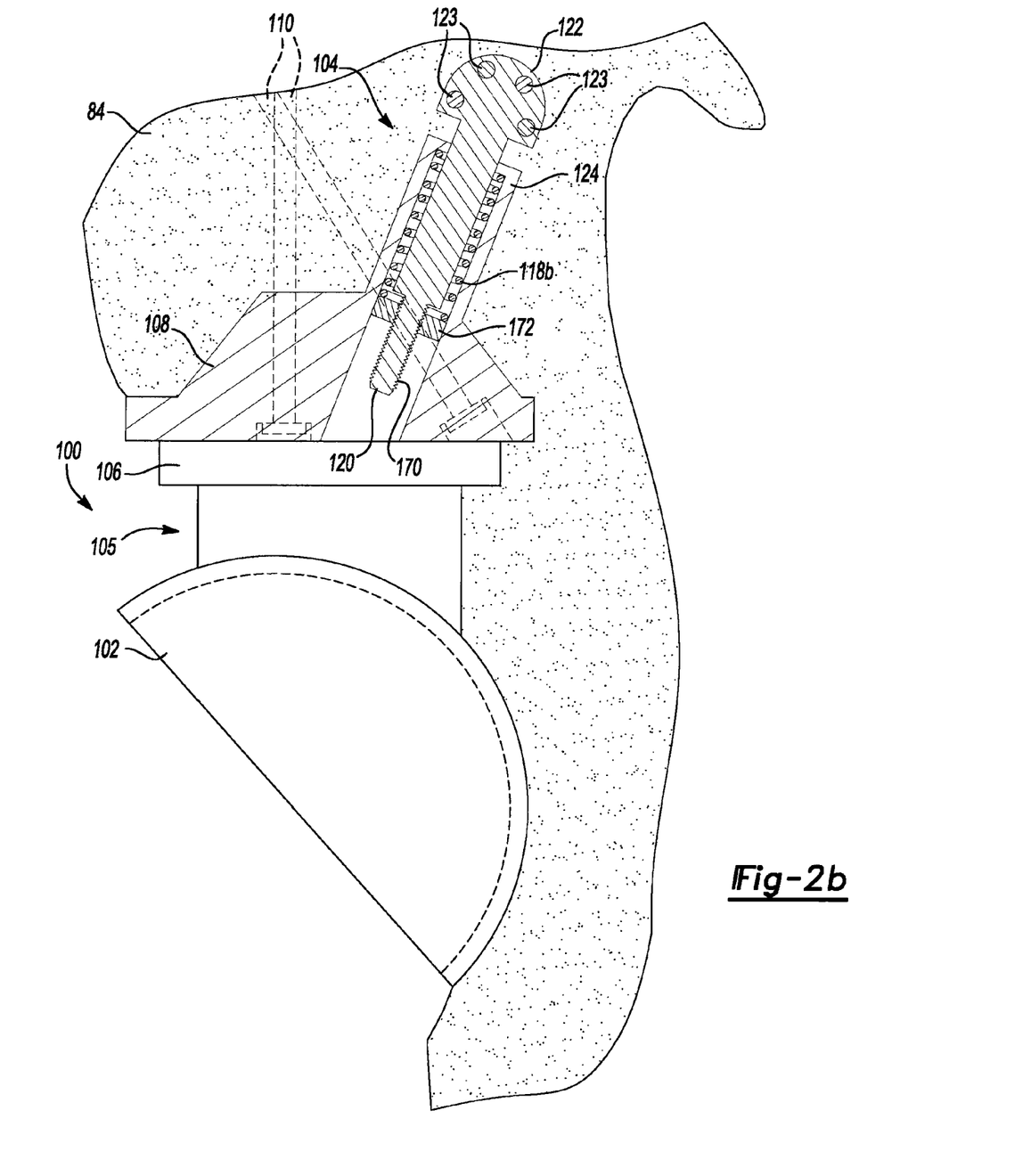

Referring to FIGS. 1b and 2b, an exemplary compliant fixator 104 can include, for example, a compliant body 118 illustrated in two exemplary aspects 118a, 118b. The compliant body 118 can be include one or more compliant elements, such as one or more Belleville washers or other spring washers 118a, as shown in FIG. 1b or a helical spring 118b, as shown in FIG. 2b. The spring 118b can be, for example, a single or double helical spring. The compliant body 118 can include an elastic bar that is more compliant relative to the surrounding bone, or any other compliant structure. The compliant body 118 can be received in a sleeve 124 and can be coupled to an anchoring portion 122 by a connecting/traction rod 120, which operates to expand or contract the compliant body 118 by a biasing mechanism. The biasing mechanism can include, for example, a nut 172 that can advanced on a threaded portion 170 of the traction rod 120 until it contacts and compresses the compliant body 118, or other supplemental interposed compliant device. The anchoring portion 122 can include apertures that can receive pins or other bone fasteners 123 for additional securement of the anchoring portion to the ilium 84, at the discretion of the surgeon in particular applications and depending on the location and orientation of the compliant fixator 104. Detailed descriptions of the structure and operation of various compliant fixators 104 and biasing mechanisms are provided in the above-referenced patents.

The acetabular component 102 can be an acetabular cup for at least partial attachment to the acetabulum 86 of the pelvis 80. The acetabular component 102 can optionally include any appropriate femoral components, such as, for example, an acetabular bearing or liner 112, a femoral head 114, and a femoral stem 116. Any of these femoral components can be integral with or modularly connected to the acetabular component 102 by known methods and devices.

The acetabular component 102 can be integrally or modularly coupled to the compliant fixator 104, directly or by using an intermediate connector 105. The connector 105 can include a plate 106 or other attachment portion for attachment to the pelvis 80. The connector 105 can be provided in various lengths to accommodate different resection situations, and/or can be modularly extended using Morse couplers, telescopic portions, slidable flanges or other length extenders. Static fixators 110, such as bone pins, screws, keels, or pegs can be optionally implanted at desired locations and orientations, in addition to the compliant fixator 104, for providing increased stability to the pelvic implant assembly 100 at particular bone locations. In some applications, such as, for example, when the pelvis 80 has an extensive weak/damaged area, the connector 105 can include a conical, spherical, rounded or otherwise shaped anchoring portion 108 extending into ilium 84 and coupled to the sleeve 124 of the compliant fixator 104 for improved anchoring. The anchoring portion 108 can be differently sized, depending on the application. Other known anchoring devices can also be optionally provided.

Figure 3:
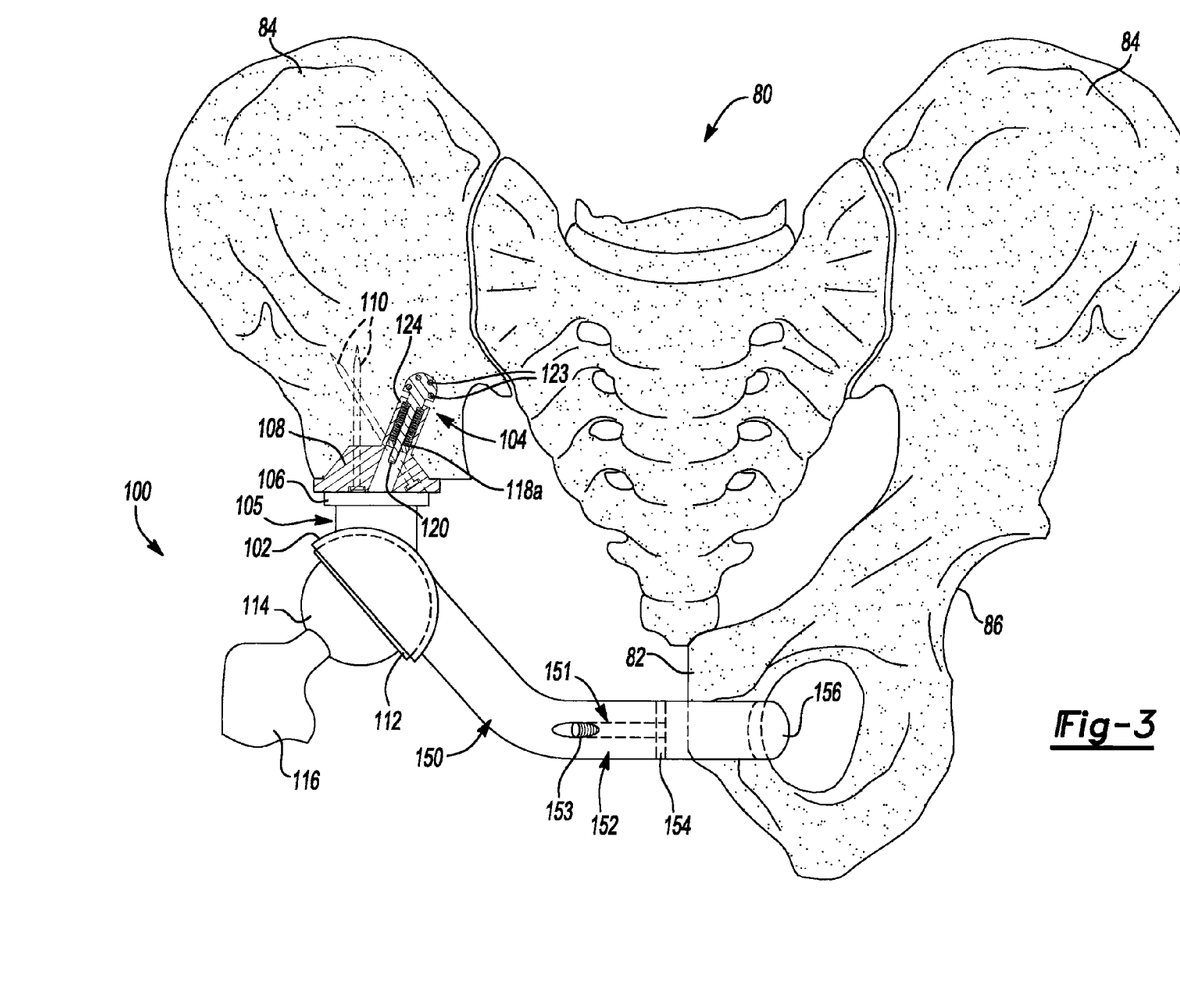
FIG. 3 is an environmental front view of a pelvic implant assembly according to the present teachings.
Figure 4:
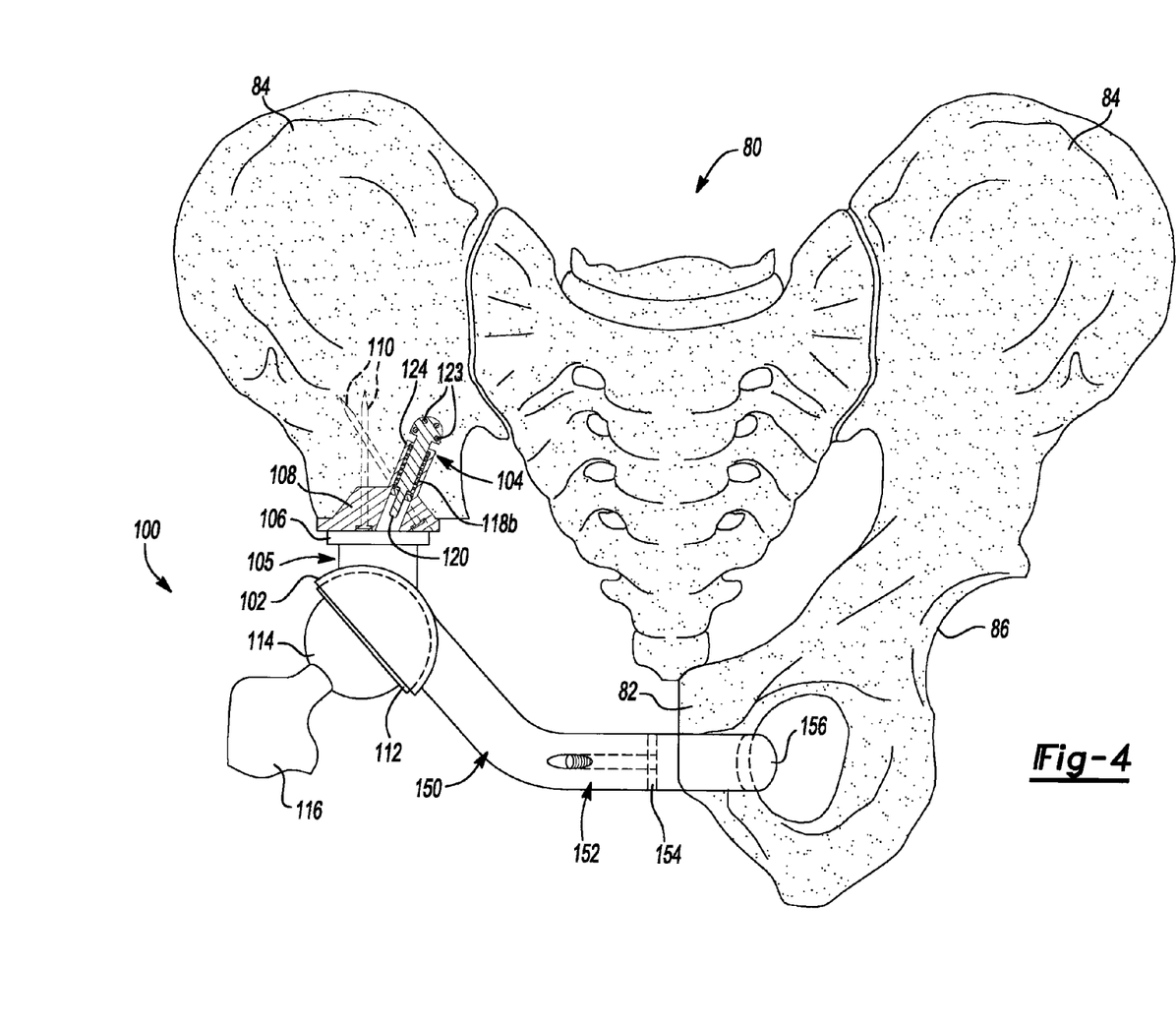
FIG. 4 is an environmental front view of a pelvic implant assembly according to the present teachings.

Referring to FIGS. 3 and 4, the pelvic implant assembly 100 can include a pubic implant 150, such as the pubic implant described in co-pending and commonly assigned U.S. patent application Ser. No. 10/838,885, the disclosure of which is incorporated by reference herein. It will be appreciated that other pubic implants 150 can also be used. The pubic implant 150 can be used, for example, when the pubic bone associated with the damaged side of the pelvis 80 is resected or missing. The pubic implant 150 can be connected to the acetabular component 102 and to the remaining (healthy) pubic bone 82 on the opposite side of the pelvis 80. The pubic implant 150 can include, for example, a clamping device 152 for clamping a portion of the pubic bone 82 between a catch plate 154 and a clamping portion 156. The clamping device 152 can include a worm-and-ratchet mechanism 151, with the catch plate 154 functioning as a ratchet and a threaded element 153 functioning as a worm. Various other clamping arrangements can be used, such as those described in U.S. patent application Ser. No. 10/838,885, or other known mechanisms.

It will be appreciated that the pelvic implant assembly 100 can be adapted for use in primary, revision, or reconstruction surgeries of the pelvis 80, and in situations with variable extent of damage. The pelvic implant assembly 100 can be integrally constructed in various conventional sizes or customized for a particular patient. The pelvic implant assembly 100 can also be partially or fully modular, affording the surgeon the option to select appropriate components based on the extent of the ilium and pubic bone damage. The pelvic implant assembly 100 can be adapted to provide the desired degree of dynamic load to promote bone growth and stabilize the pelvic implant. Various compliant components with integrated or separate bone anchoring devices and fasteners can be used.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A pelvic implant assembly comprising:
   an acetabular cup at least partially attachable to an acetabulum of the pelvis;
   an acetabular bearing coupled to an inner surface of the acetabular cup; and
   a compliant fixator implantable into the pelvis, the compliant fixator coupled to an outer surface of the acetabular cup, the compliant fixator including:
      a sleeve;
      a biasing element received and contained within the sleeve; and
      a biasing mechanism operable to expand and contract the biasing element and provide a dynamic load to the pelvis, wherein the biasing element includes a plurality of Belleville washers, and the biasing mechanism includes a nut threadable on a portion of a traction rod axially passing through the sleeve and engageable to the pelvis;
   a connector coupling the compliant fixator and the acetabular cup; and
   a plate coupled to the connector.

2. The pelvic implant assembly of claim 1, further comprising a curved surface coupling the connector and the compliant fixator.

3. The pelvic implant assembly of claim 1, further comprising a conical surface coupling the connector and the compliant fixator.

4. The pelvic implant assembly of claim 1, further comprising a prosthetic femoral head articulating with the acetabular bearing.

5. The pelvic implant assembly of claim 4, further comprising a prosthetic femoral stem coupled to the femoral head.

6. The pelvic implant assembly of claim 1, further comprising a pubic implant for coupling the acetabular cup to an opposing pubic bone.

7. The pelvic implant assembly of claim 6, wherein the pubic implant comprises a clamping device for clamping a portion of the pubic bone.

8. A pelvic implant assembly comprising:
   an acetabular cup at least partially attachable to an acetabulum of the pelvis;
   an acetabular bearing coupled to an inner surface of the acetabular cup;
   a compliant fixator implantable into the pelvis, the compliant fixator coupled to an outer surface of the acetabular cup, the compliant fixator including:
      a sleeve;
      a biasing element received and contained within the sleeve; and
      a biasing mechanism operable to expand and contract the biasing element and provide a dynamic load to the pelvis, wherein the biasing element is a helical spring, and the biasing mechanism includes a nut threadable on a portion of a traction rod axially passing through the sleeve and engageable to the pelvis;

a connector coupling the compliant fixator and the acetabular cup; and a plate coupled to the connector.

9. The pelvic implant assembly of claim 8, further comprising at least one bone fixator for coupling the connector to the pelvis.

10. The pelvic implant assembly of claim 8, further comprising a prosthetic femoral head articulating with the acetabular bearing.

11. A pelvic implant assembly comprising:

an acetabular cup having an outer bone-engaging surface and an inner bearing-engaging surface, the outer surface at least partially attachable to an acetabulum of the pelvis;

an acetabular bearing coupled to the inner surface of the acetabular cup;

a prosthetic femoral head articulating with the acetabular bearing;

a prosthetic femoral stem coupled to the prosthetic femoral head; and a compliant fixator implantable into the pelvis and providing dynamic load to the pelvis, the compliant fixator including:

a sleeve;

a traction rod axially passing through the sleeve and engageable to the pelvis;

a helical spring coupled to the traction rod and received and contained within the sleeve; and a nut threadably movable on a portion of the traction rod for compressing the helical spring;

a connector coupling the compliant fixator to an outer surface of the acetabular cup; and a plate coupled to the connector.

\* \* \* \* \*

UNITED STATES PATENT AND TRADEMARK OFFICE
CERTIFICATE OF CORRECTION

PATENT NO.        : 7,476,254 B2
APPLICATION NO.   : 11/326561
DATED             : January 13, 2009
INVENTOR(S)       : White et al.

It is certified that error appears in the above-identified patent and that said Letters Patent is hereby corrected as shown below:

Column 2
Line 57, delete "be".

Column 3
Line 1, insert --be-- before "advanced".

Signed and Sealed this

Twenty-first Day of April, 2009

JOHN DOLL
*Acting Director of the United States Patent and Trademark Office*